US011236375B2

United States Patent
Tachaapaikoon et al.

(10) Patent No.: US 11,236,375 B2
(45) Date of Patent: Feb. 1, 2022

(54) **MUTANT STRAIN *CLOSTRIDIUM THERMOCELLUM* FOR PRODUCING CELLULASE AND XYLANASE AND PREPARATION METHOD THEREOF**

(71) Applicant: PTT Global Chemical Public Company Limited, Bangkok (TH)

(72) Inventors: Chakrit Tachaapaikoon, Bangkok (TH); Khanok Ratanakhanokchai, Bangkok (TH); Patthra Pason, Bangkok (TH); Rattiya Waeonukul, Bangkok (TH); Prattana Ketbot, Bangkok (TH); Wikanda Techanan, Bangkok (TH); Kraileark Kittisuriyanont, Bangkok (TH); Narong Kaewsuwan, Bangkok (TH)

(73) Assignee: PTT Global Chemical Public Company Limited, Bangkok (TH)

(*) Notice: Subject to any disclaimer, the term of this patent is extended or adjusted under 35 U.S.C. 154(b) by 0 days.

(21) Appl. No.: 16/620,242

(22) PCT Filed: May 30, 2018

(86) PCT No.: PCT/TH2018/000028
§ 371 (c)(1),
(2) Date: Dec. 6, 2019

(87) PCT Pub. No.: WO2018/226170
PCT Pub. Date: Dec. 13, 2018

(65) Prior Publication Data
US 2021/0079434 A1 Mar. 18, 2021

(30) Foreign Application Priority Data
Jun. 7, 2017 (TH) .................. 1701003165

(51) Int. Cl.
*C12N 1/20* (2006.01)
*C12N 15/01* (2006.01)
(Continued)

(52) U.S. Cl.
CPC ............ *C12P 19/14* (2013.01); *C12N 1/20* (2013.01); *C12N 9/2437* (2013.01);
(Continued)

(58) Field of Classification Search
None
See application file for complete search history.

(56) References Cited

U.S. PATENT DOCUMENTS

2014/0373199 A1    12/2014  Zhang et al.
2021/0079434 A1*   3/2021   Tachaapaikoon ....... C12P 19/14

FOREIGN PATENT DOCUMENTS

WO    2012/153189 A2    11/2012
WO    2012153189 A2     11/2012
WO    2018/226170 A2    12/2018

OTHER PUBLICATIONS

Mori, "Isolation of mutants of Clostridium thermocellum with enhanced cellulase production", Agricultural and Biological Chemistry, vol. 54, No. 3, pp. 825-826, 1990 (Year: 1990).*
(Continued)

*Primary Examiner* — Richard C Ekstrom
(74) *Attorney, Agent, or Firm* — Troutman Pepper Hamilton Sanders LLP (57) ABSTRACT

The present invention relates to a novel mutant strain *Clostridium thermocellum* M2_15-C8 and a genetic modification process of said bacteria, wherein the mutant strain according to this invention can produce cellulase and xylanase more than the wild type. Moreover, the obtained enzymes can be used to digest the pretreated bagasse to further produce sugars effectively.

15 Claims, 3 Drawing Sheets

(51) Int. Cl.
*C12P 19/02* (2006.01)
*C12P 19/14* (2006.01)
*C12N 9/42* (2006.01)
*C12N 9/24* (2006.01)

(52) U.S. Cl.
CPC ........... *C12N 9/2482* (2013.01); *C12N 15/01* (2013.01); *C12P 19/02* (2013.01); *C12Y 302/01004* (2013.01); *C12Y 302/01008* (2013.01)

(56) References Cited

OTHER PUBLICATIONS

Mendez et al., "Isolation of Clostridium thermocellum auxotrophs", Applied and Environmental Microbiology, vol. 43, No. 2, pp. 495-496, 1982 (Year: 1982).*

Tailliez et al., "Cellulose fermentation by an asporogenous mutant and an ethanol-tolerant mutant of Clostridium thermocellum", Applied and Environmental Microbiology, vol. 55, No. 1, pp. 203-206, 1989 (Year: 1989).*

Tailliez et al. 'Enhanced Cellulose Fermentation by an Asporogenous and Ethanol-Tolerant Mutant of Clostridium Thermocellum' Applied And Environmental Microbiology, 1989, vol. 55, No. 1, pp. 207-211; abstract; p. 211, col. 1, first paragraph.

Yuan et al. 'Biochemical Characterization and Structural Analysis of a Bifunctional Cellulase/Xylanase from Clostridium Thermocellum' Journal of Biological Chemistry, 2015, vol. 290, No. 9, pp. 5739-5748; abstract. DOI 10.1074/jbc.M114.604454.

* cited by examiner

MUTANT STRAIN *CLOSTRIDIUM THERMOCELLUM* FOR PRODUCING CELLULASE AND XYLANASE AND PREPARATION METHOD THEREOF

TECHNICAL FIELD

Biotechnology relates to the mutant strain *Clostridium thermocellum* for producing cellulase and xylanase and preparation method thereof.

BACKGROUND OF THE INVENTION

At present, the production of biofuel and basic chemicals from lignocellulosic biomass as substitute of petroleum products gains more interests because the effective biorefinery industrials are the integration of fuel, chemicals, materials, and energy from biomass chemical compositions, including their by-products from near-zero waste process to maximize the value of raw materials. This is very interesting way in both technical and economic aspects. Therefore, the saccharification process in the production of biofuel via suitable biological and chemical processes gain more interests.

The lignocellulosic biomass comprises of three main compositions: cellulose, hemicellulose, and lignin arranging complexly and strongly. Therefore, the pretreatment process of the lignocellulosic biomass is required to break the lignin structure to produce digestible biomass.

The enzymatic saccharification of biomass is one of the digestion processes that gains many interests in order to produce sugars from biomass in the production of fuel and other biochemical substances because said process requires less extreme chemicals, temperatures, or energy, need no cofactor or other metals in catalyzing. Therefore, many interests have been paid to the enzymatic saccharification of biomass.

The saccharification process uses 2 main groups of enzyme: cellulase group and hemicellulase group. The cellulase group comprises of 3 types of enzyme: 1) endoglucanase, 2) exo-glucanase or cellobiohydrolase, and 3) β-glucosidase, which digesting cellulose to glucose.

The hemicellulase group comprises of endo-xylanase and β-xylosidase, which digesting xylan which is the main composition of hemicellulose. Moreover, there are other enzymes that digest hemicellulose, such as α-L-arabinofuranosidase, α-glucuronidase, α-galactosidase, acetyl xylan esterase, ferulicacid esterase, and β-mannanase.

The synergistic action of cellulase and hemicellulase is an important factor in the effective saccharification process. These enzymes can be divided into 2 main forms: free enzyme and cellulosome containing several enzymes. The cellulosome can be produced from anaerobic microorganisms such as *Clostridium thermocellum*, *Clostridium cellulovorans*, *Clostridium josui*, and *Clostridium cellulolyticum*.

At present, there are several methods to improve microorganisms strains such as mutant induction, recombination, and gene cloning, etc. The use of ultraviolet (UV) radiation to induce mutation in organisms is one popular method to improve strains because it is easy and highly effective. There are several patent documents and reports in the microorganisms strains improvement employing ultraviolet radiation to increase the productivity of proteins or enzymes or to increase the performance of the microbes.

CN 103409347 discloses the modified strain *Bacillus alcalophilus* CGMCC No. 7545 in order to increase the performance in the production of protease enzyme that can tolerant the basic condition. The obtained strain was *Bacillus alcalophilus* Ap180. Said strain can produce protease that can tolerant the basic condition of more than 8,000 unit/mL and has better stability under basic condition than the original strain.

CN 104630084 and CN 104630180 disclose the modification of strain *Bacillus subtilis* CGMCC 7926 that can produce amylase that tolerant the heat well by UV light modification, making this strain tolerant to acids, heat, and produce more enzyme that can be applied to several applications.

RU0002564127 discloses genetic modification using UV light to *Bacillus subtilis* that are probiotics and produce essential amino acids well to increase their stabilities in bile acids in gastronomical system to be applied in animal feed industry.

Moreover, CN 101531972 discloses the improvement of *Actinobacillus succinogenes* strain CGMCC 1593 employing UV light, producing *Actinobacillus succinogenes* strain CGMCC 2653 that can produce more succinic acid and tolerant to sodium ions better than the original strain.

WO 2012/088467A2 discloses the improvement of strain *Clostridium thermocellum* using recombination method in order to produce xylose.

Nevertheless, one problem of the enzymatic saccharification process is the high cost of producing enzyme from microorganisms. There have been attempts to study and develop microorganisms capable for producing a highly amount of enzymes. From said above-mentioned reason, the microorganims capable of producing cellulase and xylanase in the high amount can be used in large scale industry for applying enzymes to produce sugars from agricultural materials.

Moreover, from the information disclosed above, genetic modification has not been done with *Clostridium thermocellum* for producing higher cellulase and xylanase. Therefore, the present invention aims to prepare the mutant strain *Clostridium thermocellum* from ultraviolet light induction which makes said strain capable of producing high amount of cellulase and xylanase.

SUMMARY OF INVENTION

This invention relates to a novel mutant strain *Clostridium thermocellum* M2_15-C8 and a genetic modification process of said bacteria, wherein the novel mutant strain is kept at NITE Patent Microorganisms Depositary (NPMD), Japan, under accession number NITE ABP-02390.

Said mutant strain *Clostridium thermocellum* can produce cellulase and xylanase that can be used to digest the pretreated bagasse to further produce sugars effectively.

DESCRIPTION OF THE INVENTION

Definitions

Technical terms or scientific terms used herein have definitions as by an ordinary person skilled in the art unless stated otherwise.

Any tools, equipment, methods, or chemicals named here mean tools, equipment, methods, or chemicals being used commonly by an ordinary person skilled in the art unless stated otherwise that they are tools, equipment, methods, or chemicals specific only in this invention.

Use of singular noun or singular pronoun with "comprising" in claims or specification means "one" and including "one or more", "at least one", and "one or more than one".

All compositions and/or methods disclosed and claims in this application aim to cover embodiments from any action, performance, modification, or adjustment without any experiment that significantly different from this invention, and obtain with object with utility and resulted as same as the present embodiment according to an ordinary person ordinary skilled in the art although without specifically stated in claims. Therefore, substitutable or similar object to the present embodiment, including any little modification or adjustment that clearly seen by an ordinary person skilled in the art should be construed as remains in spirit, scope, and concept of invention as appeared in appended claims.

Throughout this application, term "about" means any number that appeared or showed here that could be varied or deviated from any error of equipment, method, or personal using said equipment or method.

Hereafter, the invention embodiments are shown without any purpose to limit any scope of the invention.

The present invention relates to the *Clostridium thermocellum* M2_15-C8 strain being genetically modified by ultraviolet light induction in order to produce novel strain that capable for producing highly amount of cellulase and xylanase, including method of genetic modification and the use of obtained enzymes in saccharification of biomass.

*Clostridium thermocellum* M2_15-C8 according to this invention was kept at NITE Patent Microorganisms Depositary (NPMD), Japan under the regulations of Budapest Treaty, wherein said strain was deposited on 19 Dec. 2016 under accession number NITE ABP-02390.

Term "culture" used in this invention means including liquid culture or solid culture but not limited to the said methods as long as the strain according to this invention can be cultured.

Term "saccharification" means the saccharification of cellulose and/or hemicellulose in the biomass to oligosaccharide, disaccharide, monosaccharide, or mixture thereof. In the same way, the saccharification of biomass includes the hydrolysis of glycosidic bond of poly-saccharide by cellulase and/or hemicellulase.

In one embodiment, mutant strain *Clostridium thermocellum* is produced from ultraviolet light induced genetic modification of wild type *Clostridium thermocellum*, wherein the said mutant strain is *Clostridium thermocellum* M2_15-C8.

In one aspect of the invention, the genetic modification process to obtain mutant strain *Clostridium thermocellum* can be performed by ultraviolet radiation with intensity from 40 to 100 microwatts per square centimeter to the wild type *Clostridium thermocellum* at the concentration of 0.1-1.0 grams per carbon source for the duration from 10 to 120 minutes.

Preferably, theabove-mentioned genetic modification process may be operated by ultraviolet radiation intensity from 40 to 80 microwatts per square centimeter to the wild type *Clostridium thermocellum* from 15 to 60 minutes.

In one aspect of the invention, the genetic modification process in order to obtain mutant strain *Clostridium thermocellum* is operated under anaerobic condition.

In one aspect of the invention, the genetic modification process in order to obtain mutant strain *Clostridium thermocellum* is operated twice.

In one aspect of the invention, the mutant strain *Clostridium thermocellum* M2_15-C8 obtained from the said process have nucleotide sequence of relevant gene related to the production of cellulase and xylanase groups and proteins related to transporting proteins and enzymes out of the cells different from the original as gene code: 111, 220, 419, 427, 442, 453, 850, 1252, 1257, 1305, 1456, 1529, 1884, 1902, 2246, 2479, 2611, 2654, 2701, 2854, and 2875.

In one aspect of the invention, the culturing of bacteria for genetic modification process can be performed by culturing bacteria in basic medium having a carbon source concentration in a range of 0.5-1.0% (w/v) under anaerobic condition at the temperature in a range of 55 to 65° C., preferably 60° C., for 24-96 hours.

In one aspect of the invention, the carbon source selected from, but not limited to cellulose powder, rice straw, bagasse, or mixture thereof. Preferably, the carbon source is cellulose powder.

In one aspect of the invention, the air in prepared culturing medium is removed by adding carbon dioxide gas, and being sterilized at the temperature about 110-130° C., pressure of 10-20 psi, for 15-20 minutes before inoculation.

In one aspect of the invention, the isolation of the genetically modified bacteria can be performed by: 1) culturing the genetically modified bacteria in basal medium at the conditions above-described; 2) diluting the cultured genetically modified bacteria; 3) transferring the diluted genetically modified bacteria to basal agar medium containing cellulose powder as carbon source, and then applying roll tube method and incubated at the temperature about 60° C. for about 24-48 hours; and 4) isolating the target colony wherein the isolated mutant strain *Clostridium thermocellum* M2_15-C8 is further cultured according to the culturing method above-described for further enzyme production.

In one aspect of the invention, the production process of cellulase and xylanase from the mutant strain *Clostridium thermocellum* M2_15-C8 can be performed by culturing the mutant strain *Clostridium thermocellum* M2_15-C8 in culturing medium containing carbon source. The ratio of bacteria to carbon source is in a range of 0.1-1.0 g of bacteria to g of carbon source under temperature in a range of 55-65° C. for 24-96 hours.

Preferably, the ratio of bacteria to carbon source is in the range of 0.2-0.5 g of bacteria to g of carbon source.

Preferably, the culturing operation temperature of the mutant strain *Clostridium thermocellum* M2_15-C8 for enzyme production is 60° C.

Preferably, the suitable culturing duration of the mutant strain *Clostridium thermocellum* M2_15-C8 for enzyme production is in the range of 48 to 72 hours. Most preferably, the suitable culturing duration is 72 hours.

In one aspect of the invention, the carbon source concentration in the culturing medium is in a range of 1-3% (w/v).

In one aspect of the invention, the culturing process of the mutant strain *Clostridium thermocellum* M2_15-C8 for enzyme production is operated under anaerobic condition.

In one aspect of the invention, the culturing process of the mutant strain *Clostridium thermocellum* M2_15-C8 for enzyme production selected from, but not limited to rice straw, bagasse, and mixture of rice straw and bagasse. Preferably, the used carbon source is bagasse.

In one aspect of the invention, bacteria can be isolated from culturing medium containing enzymes produced by bacteria by general isolation methods known by an ordinary person skilled in the art such as centrifugation, filtration, or relevant methods. The culturing liquid containing cellulase and xylanase can be used directly as crude enzyme.

In one aspect of the invention, the culturing liquid containing cellulase and xylanase may be further purified by any methods known by an ordinary person skilled in the art, wherein it may be used two or more purification methods together.

In one aspect of the invention, enzymes produced from the mutant strain *Clostridium thermocellum* M2_15-C8 comprising: 1) cellulolytic enzyme such as carboxy methyl cellulase, avicelase, cellobiohydrolase, and (3-glucosidase; and 2) xylanolytic enzyme such as xylanase, β-xylosidase, β-galactosidase, arabinofuranosidase, and acetylxylanesterase.

In one aspect of the invention, enzymes produced from the mutant strain *Clostridium thermocellum* M2_15-C8 can be used in the saccharification of biomass, wherein the preferably biomass is bagasse.

In one aspect of the invention, the biomass for saccharification may be in both wet and dry form.

In one aspect of the invention, the biomass for saccharification may be subjected to the pretreatment process selected from steam explosion using base catalyst method (STEX), organic solvent separation method (FR), sodium hydroxide in acetone method (AC), and sodium methoxide in methanol method (MM), wherein two or more pretreatment methods can be used prior to the enzymatic saccharification.

In one aspect of the invention, enzymes produced from the mutant strain *Clostridium thermocellum* M2_15-C8 may be used together with other enzymes as mixed enzymes in order to increase the saccharification performance of the biomass.

The following parts aim for describing the embodiments of the invention only, not for limiting the scope of this invention in any way.

Example 1: The Genetic Modification of *Clostridium thermocellum* by Ultraviolet Induction and the Selection of the Mutant Strain that Produce High Amount of Cellulase and Xylanase Basal medium containing 0.045% (w/v) of dipotassium phosphate ($K_2HPO_4$) and 0.045% (w/v) of potassium dihydrogen phosphate ($KH_2PO_4$), 0.09% (w/v) ammonium sulfate (($NH_4)_2SO_4$), 0.09% (w/v) sodium chloride (NaCl), 0.018% (w/v) magnesium sulfate heptahydrate ($MgSO_4 \cdot 7H_2O$), 0.012% (w/v) calcium chloride hydrate ($CaCl_2 \cdot 2H_2O$), 0.4% (w/v) sodium carbonate ($Na_2CO_3$), and 0.4% (w/v) yeast extract was prepared in Hungate tube containing about 0.5-1.0% (w/v) cellulose powder as a carbon source. Then, the air in said culturing medium was removed by adding carbon dioxide and being sterilized at the temperature about 120-125° C., at the pressure of 15 psi for about 15-20 minutes. The wild type *Clostridium thermocellum* KK8. 3 was cultured in prepared culturing medium and incubated at the temperature of 60° C. for 24-72 hours until cellulose powder was digested more than 90% (w/v). The obtained cells were kept for further mutation.

The obtained bacterium cells were placed under ultraviolet lamp at the intensity of 40-100 microwatts per square centimeter, with the distance from lamp of 10-30 cm for different durations from 10-120 min. Then, the radiated bacterium cells were transferred into basal medium tube containing 0.5-1.0% (w/v) cellulose powder as the carbon source and incubated at 60° C. for 24-48 hours. The obtained supernatant was tested for cellulase activity and xylanase activity and calculated for the increased enzyme activities comparing to the wild type.

From table 1, it was found that the mutant strain *Clostridium thermocellum* M1_60 could produce cellulase and xylanase higher than wild type strain about 2 and 2.5 times, respectively. Moreover, the mutant strain *Clostridium thermocellum* M1_60 had stability and were able to retain their effectiveness for the production of cellulase and xylanase after 10 generations.

Figure 1:
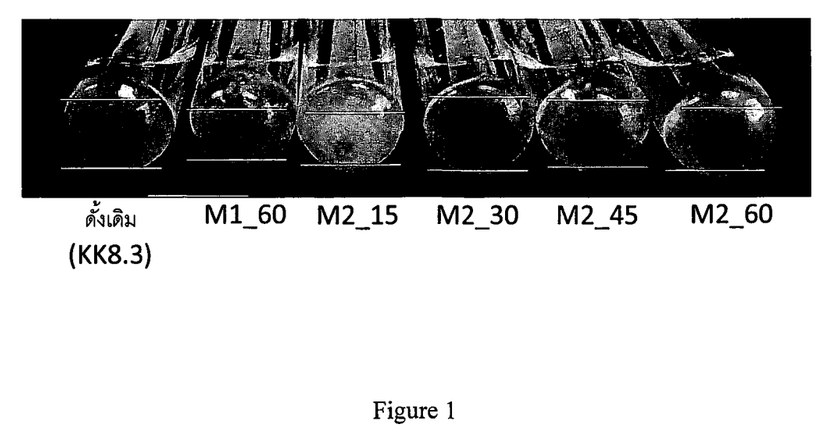
FIG. 1 shows the growth characteristic of microorgnaims and the remaining cellulose powder in medium tube of wild type *Clostridium thermocellum* KK8.3 strain and genetically modified strains.

Then, the mutant strain *Clostridium thermocellum* M1_60 were cultured in liquid basic medium containing cellulose powder as the carbon source and genetically modified with ultraviolet light according to conditions as above-described again. The growth of microorganisms and decreasing ratio of cellulose powder was shown in FIG. 1. The obtained supernatant was tested for cellulase activity and xylanase activity and calculated for the increased enzyme activities comparing the wild type and M1_60 strains. From table 1, it was found that the mutant strain *Clostridium thermocellum* M2_15 still capable of producing cellulase and xylanase higher than the wild type strain for 2 and 2.5 times respectively and were able to retain their effectiveness for the production of cellulase and xylanase after 10 generations.

TABLE 1

Comparison of cellulase activity and xylanase activity of the *Clostridium thermocellum* KK8.3 wild type and genetically modified by UV light at different conditions

| UV radiation | UV radiation time (min) | Strain | Generation | Enzyme activity (unit/mL) | | Increase of enzyme production (times) | |
| --- | --- | --- | --- | --- | --- | --- | --- |
| | | | | Cellulase | Xylanase | Cellulase | Xylanase |
| No radiation | — | KK8.3 | — | 0.29 | 0.43 | 1 | 1 |
| Cycle 1 | 60 | M1_60 | 10 | 0.59 | 1.09 | 2.03 | 2.53 |
| Cycle 2 | 15 | M2_15 | 1 | 0.60 | 1.11 | 2.07 | 2.58 |

TABLE 1-continued

Comparison of cellulase activity and xylanase activity of the *Clostridium thermocellum* KK8.3 wild type and genetically modified by UV light at different conditions

| UV radiation | UV radiation time (min) | Strain | Generation | Enzyme activity (unit/mL) Cellulase | Xylanase | Increase of enzyme production (times) Cellulase | Xylanase |
|---|---|---|---|---|---|---|---|
| Cycle 2 | 30 | M2_30 | 1 | 0.49 | 0.81 | 1.69 | 1.88 |
| Cycle 2 | 45 | M2_45 | 1 | 0.31 | 0.73 | 1.07 | 1.70 |
| Cyc;e 2 | 60 | M2_60 | 1 | 0.21 | 0.39 | 0.72 | 0.91 |

For the isolation of the mutant strain, the mutant strain *Clostridium thermocellum* M2_15 were diluted under anaerobic condition. The diluted bacteria were transferred into basal medium agar containing cellulose powder as carbon source subjected to air removal according to the methods as above-described and subjected to roll tube method to form a thin film all over the tubes. Then, the obtained culturing tubes were incubated at the temperature of 60° C. for about 24-48 hours. Then, single colony was isolated and cultured in liquid basal medium under the conditions as above-described and the colony capable of fast digestion of cellulose resulting in lower cellulose than the wild type at the same culturing time was selected.

Figure 2:
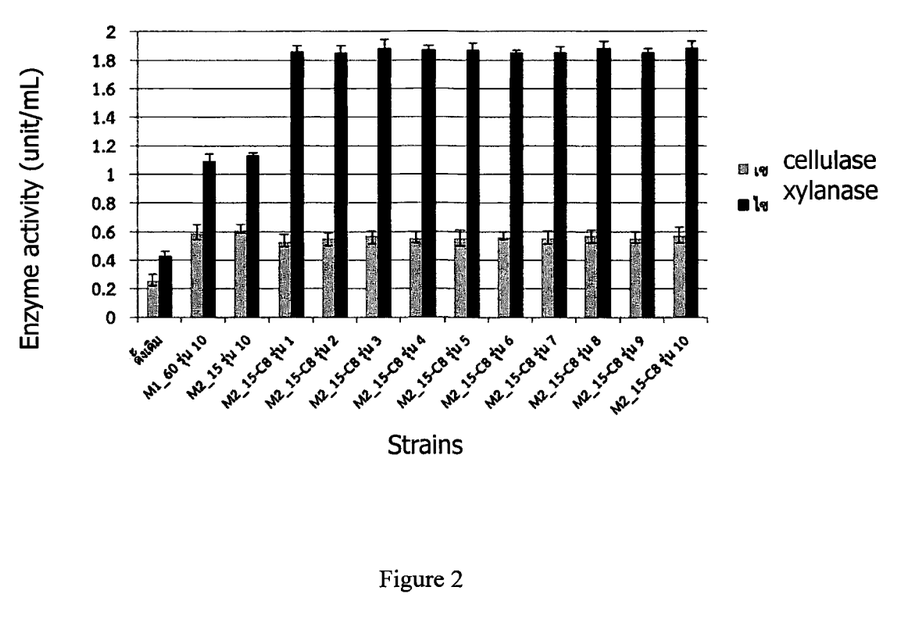
FIG. 2 shows the stability of cellulase and xylanase production from modified strain *Clostridium thermocellum* M2_15-C8 after inoculum till the $10^{th}$ generations.

From table 2, it was found that colony M2_15-C8 could digest cellulose powder faster than the wild type and produced cellulase and xylanase higher than the wild type for about 2 times and 4 times, respectively. Moreover, the *Clostridium thermocellum* M2_15-C8 were stable and could retain their productivity of cellulase and xylanase after 10 generations as shown in FIG. 2.

TABLE 2

Comparison of cellulase and xylanase activities of *Clostridium thermocellum* KK8.3 wild type and mutant strains

| Strain | Generation | Enzyme activity (unit/mL) Cellulase | Xylanase | Increase of enzyme production (times) Cellulase | Xylanase |
|---|---|---|---|---|---|
| Original | — | 0.29 | 0.43 | 1 | 1 |
| M1_60 | 10 | 0.59 | 1.09 | 2.03 | 2.53 |
| M2_15 | 10 | 0.61 | 1.13 | 2.44 | 2.62 |
| M2_15-C8 | 1 | 0.53 | 1.86 | 2.12 | 4.33 |
| M2_15-C8 | 2 | 0.55 | 1.85 | 2.20 | 4.30 |
| M2_15-C8 | 3 | 0.57 | 1.88 | 2.28 | 4.37 |
| M2_15-C8 | 4 | 0.55 | 1.87 | 2.20 | 4.35 |
| M2_15-C8 | 5 | 0.55 | 1.87 | 2.20 | 4.35 |
| M2_15-C8 | 6 | 0.56 | 1.85 | 2.24 | 4.30 |
| M2_15-C8 | 7 | 0.55 | 1.85 | 2.20 | 4.30 |
| M2_15-C8 | 8 | 0.57 | 1.88 | 2.28 | 4.37 |
| M2_15-C8 | 9 | 0.55 | 1.85 | 2.20 | 4.30 |
| M2_15-C8 | 10 | 0.57 | 1.88 | 2.28 | 4.37 |

Example 2: Physical Characters of the Mutant Strain *Clostridium thermocellum* M2_15-C8

Figure 3:
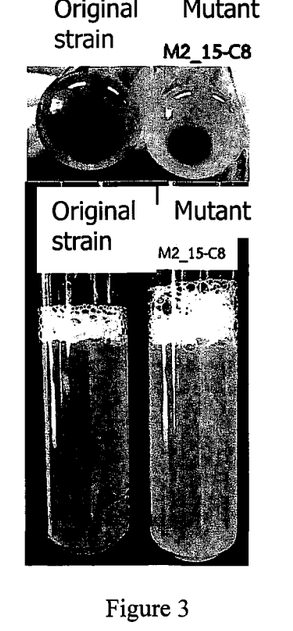
FIG. 3 shows the growth characteristic of microorganisms and the remaining cellulose powder in medium tube of wild type *Clostridium thermocellum* strain and genetically modified M2_15-C8 strains.

The mutant strain *Clostridium thermocellum* M2_15-C8 were compared their physical characters with *Clostridium thermocellum* wild type. It was found that the mutant strain *Clostridium thermocellum* M2_15-C8 have a cream-yellow in colour whereas the wild type bacteria have a strong yellow as shown in FIG. 3. Moreover, the cellulose digestion rate of the mutant strain *Clostridium thermocellum* M2_15-C8 was faster than the wild type. The mutant strain could digest 1% (w/v) cellulose powder in basic medium for more than 90% within 48 hours, whereas the wild type took more than 48 hours for digestion under the same conditions.

Example 3: Study of Proteins and Cellulase and Xylanase Characters Produced from the Wild Type and Mutant Strain *Clostridium thermocellum* M2_15-C8

The cellulase and xylanase were produced by culturing of the wild type and the mutant strain *Clostridium thermocellum* M2_15-C8 in liquid basal medium containing 1-3% (w/v) of bagasse as carbon source under anaerobic condition as above-described, following by the incubation at the temperature of 60° C. for 24-72 hours. The obtained supernatant was centrifuged at the speed higher than 8,000 rpm at the temperature of 4-10° C. for 10-20 minutes. Only the clear supernatant was concentrated by filtering through 3-10 kilodaltons membrane (Quix Stand Systems; GE life sciences) in order to obtain concentrate enzyme for further studies.

From table 3, it was found that enzymes produced from wild type and the mutant strain *Clostridium thermocellum* M2_15-C8 containing cellulolytic enzymes such as 10.21 unit/mL carboxy methyl cellulase, 2.55 unit/mL avicelase, 4.34 unit/mL cellobiohydrolase, and 2.30 unit/mL β-glucosidase, and xylolytic enzymes such as 36.85 unit/mL xylanase, 0.17 unit/mL β-xylosidase, 0.31 unit/mL β-galactosidase, 0.36 unit/mL arabinofuranosidase, and 0.31 unit/mL acetylxylanesterase. Moreover, it was found that all of the mutant strains produced all enzymes higher than the wild type. Especially, xylanase can be produced at least 4 times higher and carboxy methyl cellulase and avicelase can be produced at least 2 times higher.

Figure 4:
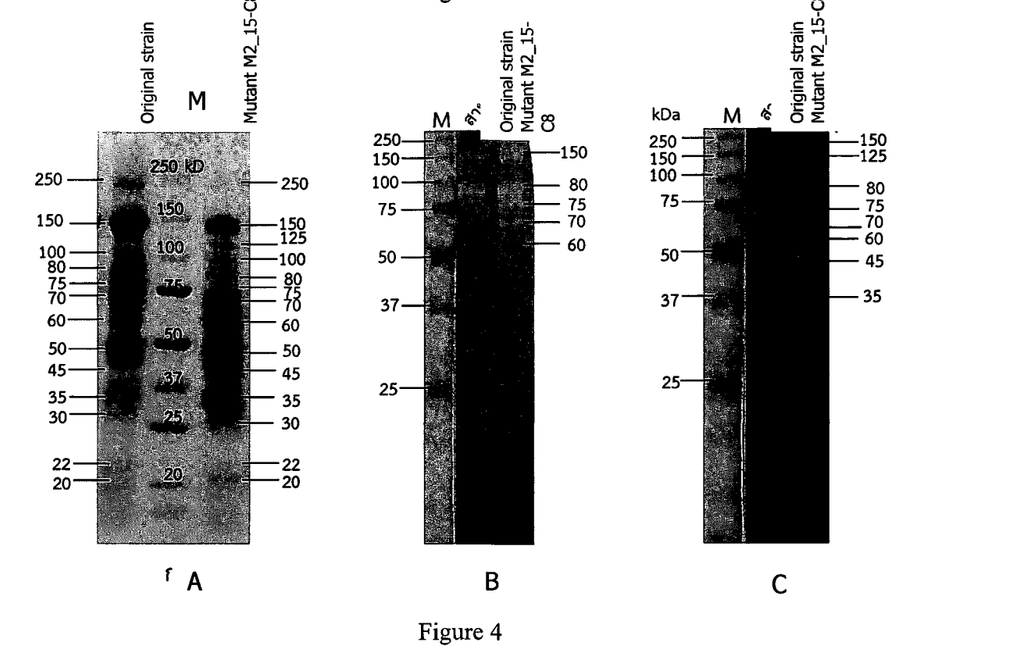
FIG. 4 shows the characteristic of proteins and enzymes produced by wild type *Clostridium thermocellum* strain and genetically modified M2_15-C8 strains: A) protein characters tested by sodium dodecyl sulphate polyacrylamide gel electrophoresis (SDS-PAGE) technique; B) cellulase characters tested by zymogram techniques; and C) xylanase characters tested by zymogram technique, wherein M means standard protein with known molecular weight and kDa means kilodalton.

FIG. 4 shows the comparison of protein characters produced by the wild type and the mutant strain *Clostridium thermocellum* M2_15-C8 using sodium dodecyl sulphate polyacrylamide gel electrophoresis (SDS-PAGE) method. It was found that at 20-250 kDa, enzymes produced by both strains had similar characters, which contain 14 proteins at 20, 22, 30, 35, 45, 50, 60, 70, 75, 80, 100, 125, 150, and 250 kDa. However, the intensity of proteins produced by both strains was different, which showed that protein amounts were different. FIG. 4a shows that the mutant strain *Clostridium thermocellum* M2_15-C8 produced more proteins at 30, 35, 45, 50, 60, 70, 100, and 125 kDa than the wild type.

Moreover, from the comparison of cellulase and xylanase characters using zymogram method as shown in FIG. 4b, cellulase characters at 20-250 kDa were similar in both strains, but some cellulase produced by the mutant strain *Clostridium thermocellum* M2_15-C8 showed higher digestion activities e.g. cellulose at 60, 70, 75, and 80 kDa. From FIG. 4c, in xylanase at 20-250 kDa, it was found that enzymes produced by both strains were similar but some xylanase produced by the mutant strain *Clostridium thermocellum* M2_15-C8 showed higher digestion activities e.g. xylanase at 35, 45, 60, 70, and 75 kDa.

TABLE 3

Enzyme activities in cellulolytic enzymes and xylolytic enzymes produced by wild type and mutant strain *Clostridium thermocellum* M2_15-C8

| Enzymes (unit/mL) | Wild type (KK8.3) | Mutant (M2_15-C8) |
| --- | --- | --- |
| Cellulolytic enzymes | | |
| Carboxy methyl cellulose | 4.64 | 10.21 |
| Avicelase | 1.24 | 2.55 |
| Cellobiohydrolase | 3.64 | 4.34 |
| β-glucosidase | 1.27 | 2.30 |
| Xylolytic enzymes | | |
| Xylanase | 9.05 | 36.85 |
| β-xylosidase | 0.13 | 0.17 |
| β-galactosidase | 0.16 | 0.31 |
| Arabinofuranosidase | 0.17 | 0.36 |
| Acetylxylanesterase | 0.29 | 0.31 |

Example 4: Comparison of Nucleotide Sequence of Genetic Materials of Wild Type and Mutant Strain *Clostridium thermocellum* M2_15-C8

The comparison of nucleotide sequence of genetic materials of wild type and mutant strain *Clostridium thermocellum* M2_15-C8 could be done by modified CTAB method. Then, about 5 μg of extracted genetic materials were searched for DNA sequencing by ion torrent sequencing method using ion personal genome machine (PGM). The obtained DNA sequencing of wild type and mutant strain *Clostridium thermocellum* M2_15-C8 were analyzed for their differences by bioinformatics method using information of *Clostridium thermocellum* ATCC27405 strain as reference genetic materials.

From the comparison of genetic materials of wild type and mutant strain *Clostridium thermocellum* M2_15-C8, it was found that cellulolytic and xylolytic enzymes producing genes and proteins related to transportation of proteins and enzymes outside their cells were mutated for at least 21 genes as shown in table 4. Two mutation areas were at 500 bases before CDS and at coding sequence (CDS).

From table 4, according to the mutation at 500 bases before CDS, the nucleotide sequences of gene codes 220, 427, 453, 850, 1252, 1257, 1305, 1884, and 1902 were missing, whereas the nucleotide sequences of gene code 2701 were increased. This was because the 500 bases before CDS contained regulator gene, promoter gene, and operator gene. Therefore, mutations at this area affected the different expression of proteins and enzymes.

Moreover, according to the mutation at the CDS, the nucleotide sequences of gene codes 111, 419, 442, 1456, 1529, 2246, 2479, 2611, 2654, 2854, and 2875 were missing. Because the CDS is the area that responded for the production of proteins or enzymes, the mutations at this area affected the different expression of proteins and enzymes.

Therefore, the mutation in genes responded for the production of cellulolytic and xylolytic enzymes, including proteins related to transportation of proteins and enzymes outside their cells affected different expressions, activities, and characters of cellulolytic and xylolytic enzymes as shown in example 3.

TABLE 4

Genes related to the production of cellulolytic and xylolytic enzymes and proteins related to transportation of proteins and enzymes outside their cells of the wild type and mutant strain *Clostridium thermocellum*

| Mutation area | Gene code | Wild type | Mutant M2_15-C8 | Role of expression proteins |
| --- | --- | --- | --- | --- |
| 500 bases before CDS | 220 | GT | G | β-glucosidase enzymes and related to digestion of cellulose |
| | 427 | CA | C | Cellulose enzymes and related to digestion of polysaccharides |
| | 453 | AT | A | Hydrolase enzymes with bonding site with bacterium cell wall |
| | 850 | ATT | A | Cellulase, mannanase, and β-mannosidase enzymes and related to digestion of polysaccharides |

TABLE 4-continued

Genes related to the production of cellulolytic and xylolytic enzymes and proteins related to transportation of proteins and enzymes outside their cells of the wild type and mutant strain *Clostridium thermocellum*

| | | Mutated nucleotide characters | | |
|---|---|---|---|---|
| Mutation area | Gene code | Wild type | Mutant M2_15-C8 | Role of expression proteins |
| | 1252 | TTA | T | MFS transporter, bacterium cell wall protein, related to transporting proteins and enzymes outside their cells |
| | 1257 | CT | C | Bacterium cell wall proteins |
| | 1305 | GT | G | β-glucosidase enzymes and related to digestion of cellulose |
| | 1884 | CT | C | ABC transporter, bacterium cell wall protein, related to transporting proteins and enzymes outside their cells |
| | 1902 | TA | T | Xylanase, β-xylosidase enzymes and related to digestion of xylan |
| | 2701 | A | AGAT | Xylanase enzymes and related to digestion of xylan |
| Coding sequence (CDS) | 111 | AT | A | Dockerin, binding protein of digesting enzymes and bacterium cell wall, supporting polysaccharide digestion of enzymes |
| | 419 | TA | T | Cellulase and β-cellobiosidase enzymes |
| | 442 | CT | C | Dockerin, binding protein of digesting enzymes and bacterium cell wall, supporting polysaccharide digestion of enzymes |
| | 1456 | AT | A | β-glucosidase enzymes and related to digestion of cellulose |
| | 1529 | CT | C | ABC transporter, bacterium cell wall protein, related to transporting proteins or enzymes outside their cells |
| | 2246 | TC | T | Proteins related to binding of carbohydrates |
| | 2479 | CT | C | Proteins related to binding of cellulose |
| | 2611 | CA | C | α-L-arabinofuranosidase enzymes and related to digestion of arabinan |
| | 2654 | CA | C | Xylanase enzymes and related to digestion of xylan |
| | 2854 | AT | A | ABC transporter, bacterium cell wall protein, related to transporting proteins and enzymes outside their cells |
| | 2875 | GA | G | Cellulase enzymes and related to digestion of polysaccharides |

Figure 5:
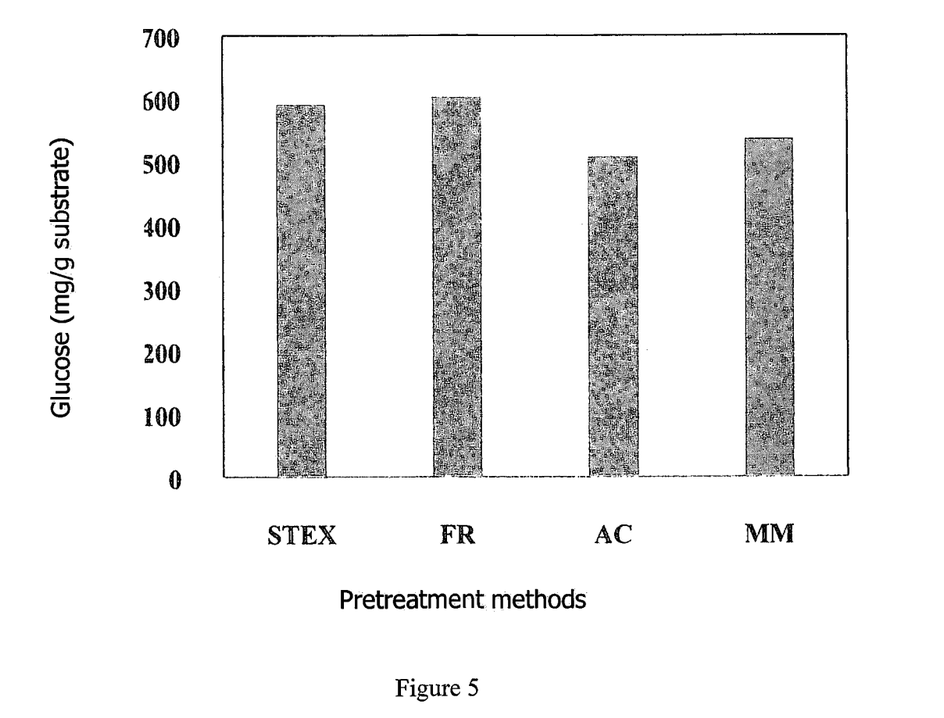
FIG. 5 shows glucose content obtained from digestion of bagasse treated with different methods using enzymes from mutant strain *Clostridium thermocellum* M2_15-C8.

Example 5: The Use of Enzymes Produced by the Mutant Strain *Clostridium thermocellum* M2_15-C8 in the Saccharification of Bagasse Bagasse pretreated with several methods such as: 1) steam explosion using base catalyst method (STEX); 2) organic solvent separation method (FR); 3) sodium hydroxide in acetone method (AC); and 4) sodium methoxide in methanol method (MM) was saccharified at the concentration of 5.0-10.0% (w/v) and pH about 6.0 to 7.0 was added with enzymes produced by the mutant strain *Clostridium thermocellum* M2_15-C8 according to example 3. The concentration of enzymes was about 10-20 mg/g bagasse. The recombinant β-glucosidase were also added at the concentration about 10-30 unit/g bagasse into the mixture. The mixture was incubated at the temperature 50-60° C. for 12-48 hours. Then, the obtained glucose was subjected to quantitative analysis. It was found that enzymes produced by mutant strain, together with recombinant β-glucosidase could saccharify bagasse pretreated by steam explosion method and produced glucose more than 590 mg/g substrate, could saccharify bagasse pretreated by composition separation with organic solvent method and produced glucose more than 600 mg/g substrate, and could saccharify bagasse pretreated by sodium hydroxide in acetone method and produced glucose more than 500 mg/g substrate. Moreover, they could saccharify bagasse pretreated by sodium methoxide in methanol method and produced glucose more than 530 mg/g substrate as shown in FIG. 5.

Preferred Embodiment of the Invention

Preferred embodiment of the invention is as provided in the description of the invention.

The invention claimed is:

1. A mutant strain *Clostridium thermocellum*, wherein said mutant strain *Clostridium thermocellum* is *Clostridium thermocellum* M2_15-C8, accession number NITE ABC-02390.

2. A genetic modification process to produce the mutant strain *Clostridium thermocellum* according to claim 1, wherein said genetic modification process comprises applying an ultraviolet radiation intensity from 40 to 100 microwatts per square centimeter to the wild type *Clostridium thermocellum* for 10 to 120 minutes.

3. The genetic modification process according to claim 2, wherein said genetic modification process comprises applying an ultraviolet radiation intensity from 40 to 80 microwatts per square centimeter to the wild type *Clostridium thermocellum* for 15 to 60 minutes.

4. The genetic modification process according to claim 2, wherein said genetic modification process is operated under anaerobic conditions.

5. The genetic modification process according to claim 2, wherein said genetic modification process is operated twice.

6. A production process of cellulase and xylanase comprising a step of cultivating of the mutant strain *Clostridium thermocellum* according to claim 1 in a carbon source, wherein the bacteria to carbon source ratio is in a range of 0.1 to 1.0 g bacteria to g carbon source under a temperature of 55-65° C. for 24-96 hours.

7. The production process of cellulase and xylanase according to claim 6, wherein the bacteria to carbon source ratio is in the range of 0.2 to 0.5 g bacteria tog carbon source.

8. The production process of cellulase and xylanase according to claim 6, wherein the carbon source is selected from cellulose powder, rice straw, bagasse, or a mixture thereof.

9. The production process of cellulase and xylanase according to claim 8, wherein the carbon source is bagasse.

10. The production process of cellulase and xylanase according to claim 6, wherein said production process is operated at a temperature of 60° C.

11. The production process of cellulase and xylanase according to claim 6, wherein said production process is operated in the range of 48-72 hours.

12. The production process of cellulase and xylanase according to claim 11, wherein said production process is operated for about 72 hours.

13. The production process of cellulase and xylanase according to claim 6, wherein said production process is operated under anaerobic conditions.

14. A method of saccharification of biomass, comprising contacting the biomass with an enzyme produced by the process of claim 6.

15. The method of claim 14 wherein the biomass is bagasse.

* * * * *

UNITED STATES PATENT AND TRADEMARK OFFICE
CERTIFICATE OF CORRECTION

| | |
|---|---|
| PATENT NO. | : 11,236,375 B2 |
| APPLICATION NO. | : 16/620242 |
| DATED | : February 1, 2022 |
| INVENTOR(S) | : Chakrit Tachaapaikoon et al. |

It is certified that error appears in the above-identified patent and that said Letters Patent is hereby corrected as shown below:

In the Claims

Column (12); Line (54-55) replace "NITE ABC-02390" with "NITE BP-02390."

Signed and Sealed this
Thirtieth Day of August, 2022

Katherine Kelly Vidal
*Director of the United States Patent and Trademark Office*